(12) United States Patent
Pinnock et al.

(10) Patent No.: US 9,393,274 B2
(45) Date of Patent: Jul. 19, 2016

(54) CONTROL OF SUCKING LICE

(75) Inventors: Dudley Edwin Pinnock, Glen Osmond (AU); David John Cooper, Kingscote (AU)

(73) Assignee: Ectotec Pty Ltd (AU)

( * ) Notice: Subject to any disclaimer, the term of this patent is extended or adjusted under 35 U.S.C. 154(b) by 1844 days.

(21) Appl. No.: 11/908,480

(22) PCT Filed: Mar. 7, 2006

(86) PCT No.: PCT/AU2006/000286
§ 371 (c)(1),
(2), (4) Date: Jun. 24, 2009

(87) PCT Pub. No.: WO2006/096905
PCT Pub. Date: Sep. 21, 2006

(65) Prior Publication Data
US 2010/0135972 A1    Jun. 3, 2010

(30) Foreign Application Priority Data
Mar. 14, 2005  (AU) .................................. 2005901229

(51) Int. Cl.
*A61K 35/66* (2015.01)
*A61K 35/742* (2015.01)

(52) U.S. Cl.
CPC .................................... *A61K 35/742* (2013.01)

(58) Field of Classification Search
CPC ............ C12R 1/07; C12R 1/075; C12R 1/085
USPC ........................................ 424/93.46, 93.461
See application file for complete search history.

(56) References Cited

U.S. PATENT DOCUMENTS

| 5,273,746 A | 12/1993 | Payne et al. |
| 5,849,870 A | 12/1998 | Warren et al. |
| 5,888,801 A | 3/1999 | Warren et al. |

FOREIGN PATENT DOCUMENTS

| AU | 588849 A1 | 9/1989 |
| AU | 2003100445 A4 | 8/2003 |
| WO | WO 00/45641 | 8/2000 |

*Primary Examiner* — Ruth Davis
(74) *Attorney, Agent, or Firm* — Akerman LLP

(57) ABSTRACT

The invention describes the use of a microbial preparation of one or more bacteria, for example of the genus *Bacillus* in the manufacture of a formulation as a medicament for the treatment and prevention of infestation of sucking lice from the order Phthiraptera, Anoplura, Rhynchophthirina and/or Pediculidae. The medicament can be applied to plumage, pelage or hair to control sucking lice.

5 Claims, 1 Drawing Sheet

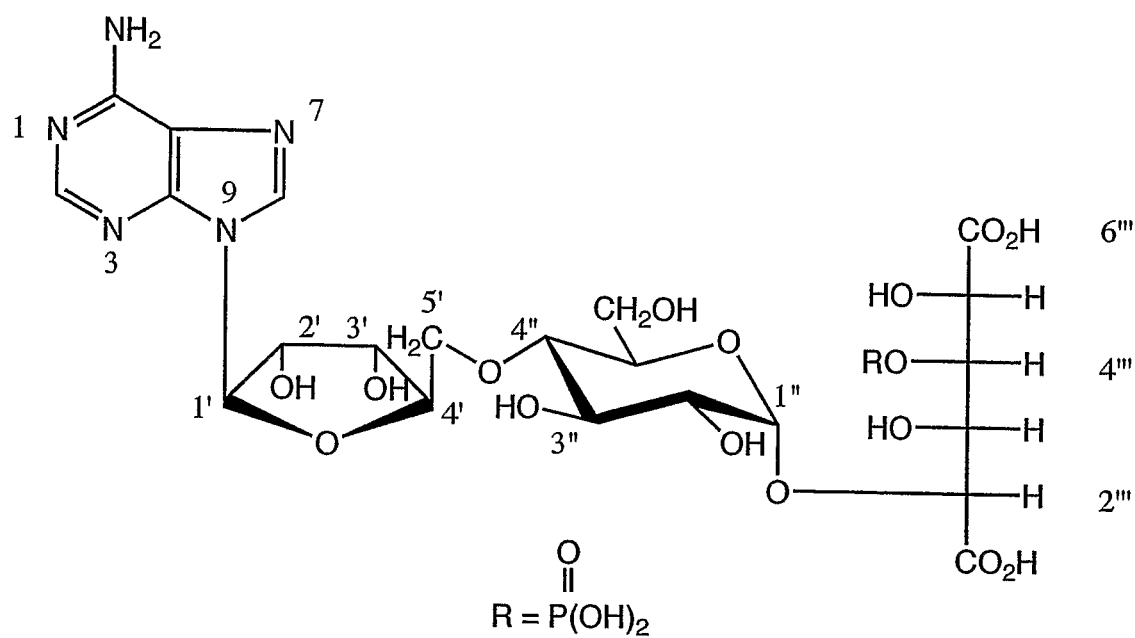
$C_{22}H_{32}N_5O_{19}P$    Mol. Wt.: 701.49

CONTROL OF SUCKING LICE

FIELD OF THE INVENTION

This new invention relates to a composition and method of control of parasitic sucking lice populations, and in particular to the control of parasitic sucking lice on humans, animals and birds Parasitic sucking lice feed on the blood, serum or lymph of their hosts and cause irritation, pruritis and disease. Some species are vectors of serious diseases and all are generally undesirable. For example, the common human head louse, *Pediculus capitis* (=*Pediculus humanus capitis*) and the human pubic louse *Phthirus pubis* are blood sucking ectoparasites which cause pediculosis disease, producing hives-like irritation and pruritis in infested patients. The human body louse, *Pediculus humanus corporis* (=*P. humanus*) causes irritation and pruritis and is also a vector of typhus—a potentially lethal disease.

Other species of ectoparasitic sucking lice also are potential carriers of disease organisms, and remain a threat to livestock, especially in intensive animal production units, stables and poultry houses and the like.

Ectoparasitic sucking lice are the cause of suffering and even death of infested animals and birds, and cause heavy economic costs in the livestock industries.

For example, according to Lapage (1962)*

"The chief effects of sucking lice on their hosts are due to the irritation they cause. They are most numerous in winter when the hosts, because they are suffering from cold, may be in closer contact, and a reduced diet at this season also favours infestation. The hosts become restless and do not feed or sleep well and they may injure themselves or damage their feathers, hair or wool by biting and scratching the parts of their bodies irritated by the sucking lice.

The resulting loss of condition may render them more susceptible to bacterial and other diseases. The egg production of birds and the milk production of cattle may fall. In mammalian hosts scratching may produce wounds or bruises on the animals, while in sheep the wool is damaged and it is also soiled by the faeces of the sucking lice. The coat becomes rough and shaggy, and if the irritation is severe, the hair may become matted.

Excessive licking by calves may lead to the formation of hair balls in the stomach. The foot louse of sheep is found most frequently around the dew claws and severe infections may produce lameness. *Haematopinus suis* may spread swine fever by passing from a dead pig to healthy ones."

Lapage, Geoffrey. (1962). Monnig's Veterinary Helminthology and Entomology. Fifth Edition, Balliere, Tindall and Cox, 7 & 8 Henrietta Street, London. 600 pp.

As used herein, the terms "human lice", and "human louse" refer to a member of order of Phthiraptera, more specifically the sub order Anoplura of the family Pediculidae, which includes *Pediculus humanus corporis, Pthirus pubis*, and *Pediculus humanus capitis*.

Head lice, *Pediculus humanus* capitis in particular, have the ability to propagate at a high rate, females lice can lay many eggs. Lice infestations are most serious in areas where hygienic standards are substandard, however, even when hygienic standards are high, head lice can still pose a significant problem, especially in children's play groups, kindergartens and boarding schools.

PRIOR ART METHODS OF HEAD LOUSE CONTROL

Chemical Methods

The prior art methods of sucking lice control used heretofore have proved only partially effective. At present, these consist of the application to the infested human, animal or bird of various preparations of toxic organophosphate (maldison, malathion), synthetic pyrethroid, synergized pyrethrins, neem and/or other plant oils, all of which are chemical pesticides of varying efficacy. In addition to the direct toxic effects such as dermal rashes, irritations or pruritis on the host to which they are applied, some of these chemicals may create a serious health hazard to the families of infested persons and to keepers, farmers and pest control personnel using them. Given that the rate of infestation by head lice (*Pediculus humanus* capitis) is greatest in young school children, whose body weights are typically less than 50 kg, it will be apparent that the application of these toxic chemicals is not a preferred method of treatment to employ.

The prior art methods of controlling parasitic sucking lice on humans include the exposure of the patient to chemical insecticides such as malathion, permethrin, pyrethrins synergised by piperonyl butoxide, and bioallethrin. (Medicines Evaluation Committee Report (2003) "A Review of the Regulation of Head Lice Treatments in Australia" Australian Government Therapeutic Goods Administration, Canberra, Australia). The shortcomings and disadvantages of these treatments are listed in the above publication and are described below:—

Treatment with malathion requires prolonged exposure of the infested person or child to the insecticide for several hours, and serious adverse effects have been observed, also the possibility recorded that lack of efficacy may be due to resistance in the lice populations to malathion (Medicines Evaluation Committee Report (2003).

Permethrin, synergized pyrethrins and bioallethrin treatments for control of human head lice have been found to cause a low incidence of adverse effects, mainly pruritis or skin rash, however there is concern that lower treatment efficacy of these chemicals may be due to insecticide resistance in the lice populations (Medicines Evaluation Committee Report (2003)"

Blends of herbal extracts and essential oils (such as Melaleuca oil, Eucalyptus oil, Lavendula oil, rosemary oil, geranium oil, thyme oil, citronella oil, anise oil, lemon oil, lemongrass oil with or without extracts of *Echinacea, purpura, Adhatoda vasica, Stemona sessifolia*) etc. are sold for the reduction of human head lice infestations in Australia and more than 20 herbal blend products are listed by the Australian Therapeutic Goods Administration. However, there is inadequate evidence to demonstrate any acceptable level of efficacy of these herbal blends for control of head lice (Medicines Evaluation Committee Report (2003). Moreover, high concentrations of some of the above oils can cause skin irritation, stinging or burning, and these herbal products cannot be automatically assumed to be safe (Medicines Evaluation Committee Report (2003).

The shortcomings and disadvantages of the above treatments are well known and have led to a global search for alternative treatments which are effective and safe for the patient. The search for new head lice treatments include:—

1. In vitro studies on the effect on head lice of two hours' exposure to the veterinary flea treatments, imidacloprid and fipronil, The results of these studies were that even at a concentration of 0.25%, fipronil produced only 97% head lice mortality after the two hours' exposure. The lack of efficacy was suggested by the authors of the study possibly to be due to cross resistance in the head lice between fipronil and lindane, because lindane resistance was demonstrated in the head lice population. (Medicines Evaluation Committee Report (2003)"

2. In another study, an oral dose of 3.5 mg/kg of levamisole (an anthelmintic) was administered once daily for ten days to 28 girls aged 7 to 12 years. An efficacy of only 67% was recorded, despite this prolonged exposure and high dosage of the chemical. (Medicines Evaluation Committee Report (2003)"
3. The oral administration to ten patients of a minimum of 80 mg trimethoprim/400 mg sulfamethoxazole twice daily for at least three days was necessary to achieve acceptable efficacy for control of head lice. In another study, an oral dose of trimethoprin/sulfamethoxazole at the rate of 10 mg/kg/day trimethoprim equivalent for ten days was compared to a 1% permethrin topical treatment retreated after 7 days, or a combination of both treatment strategies for control of head lice. The trimethoprin/sulfamethoxazole treatment gave only 78% efficacy, the permethrin treatment 72% efficacy and the combined treatments gave 92.5% efficacy as measured at the 4 week follow-up examination. There were serious adverse effects noted in this tria these included allergic reactions nausea, vomiting and transient pruritis caused by the trimethoprin/sulfamethoxazole. (Medicines Evaluation Committee Report (2003)"
4. The efficacy for control of head lice of an oral dose of trimethoprin/sulfamethoxazole at the rate of 8 mg/kg/day trimethoprim equivalent for 12 days combined with to a topical application of a 1% lindane shampoo was compared to the efficacy of the lindane shampoo alone. At the week 2 follow-up the efficacy for control of head lice was 76.8% for the lindane treatment and 86.7% for the combined treatment on retreatment the efficacy rates were 91.3% and 97.8% respectively.

Aside from the lack of efficacy and adverse patient reactions demonstrated in these experimental treatments, it seems unlikely that parents or careers would welcome the requirement to orally dose their children with a significant quantity of chemical insecticide for as long as 12 days.'

In addition to the above limitations of the prior art, chemical methods of sucking lice control, the use of these chemical pesticides is generally unsound due to the imperfect and short term protection which they provide and to the evolution of resistance by the sucking lice to the toxic effects of these chemicals.

Other methods of control of sucking lice include the use of electric combs that kill the lice by electrocution. This is commonly used in the treatment of human head lice, *Pediculus humanus* capitis. In order for this method to be even moderately effective, the combing must be diligent and continual, and it is apparent that only those lice coming into contact with the comb are removed or killed.

Microbial Methods

The use of microbial preparations for control of sheep lice, *Bovicola* (*Damalinia*) *ovis*, has been previously revealed by way of publication in Australian Patent AU-B-52488/86; however, sheep lice are entirely different organisms from sucking lice.

In this context, it must be clearly understood that the common terms "louse' and "lice' are not prescriptive, but convey merely that the reference is to small ectoparasites infesting a larger host. The term "lice' may include as diverse a range of ectoparasitic organisms as insects, crustaceans and cnidarian jellyfish, depending on the case under discussion. In most instances, the general term "lice" is modified by a description of the host or environment in which the ectoparasite exists. Some examples are:—

The term "Feather Lice" generally refers to phthirapterans insects such as *Menopon stramineus;*

The term "Fish Lice" generally refers to branchiuran crustaceans such as *Argulus* sp.;

The term "Sea Lice" may refer to cnidarian jellyfish such as *Linuche unquiculata*

The term "Poultry Head Lice generally refers to mallophagans such as *Cuclotogaster heterographa;*

The term "Salmon Lice' generally refers to isopod crustaceans such as *Lepeophtheirus salmonis;*

The term "Chicken Lice" generally refers to mallophagans such as *Menacanthus stramineus*.

The term "Plant Lice' generally refers to homopteran insects such as aphids, for example *Macrosiphum euphorbiae;*

The term "Cod Lice" refers to copepod crustaceans such as *Scolopsis bilineatus*

The term "Sheep Lice" generally refers to mallophagans such as *Bovicola ovis*

"Sucking Lice", the subject of this application, are distinctly different and separate organisms and accordingly are classified in a separate SubOrder, the Anoplura, and feed on blood. It is generally agreed that sucking lice are a distinct and different group of organisms from other "lice" and this is reflected in their separate scientific classification (reviewed and referenced, for example, by Vincent S, Smith Entomologische Abhandlungen 61:(2) 150-151.

As used herein, the term "sucking lice" or "sucking louse" refer to a member of the SubOrder Anoplura including but not confined to, the family Pediculidae, which includes the human body louse, *Pediculus humanus humanus*, and the human head louse, *Pediculus. humanus capitis*. and the human pubic louse *Pthirus pubis,*

The present invention is more particularly directed toward the control of Pediculosis, the disease, caused by the infestation of sucking lice on humans, and of diseases of animals and birds, caused by sucking lice.

OBJECT OF THE INVENTION

The object of this invention is to instruct a novel method which overcomes some of the prior art disadvantages, and which is effective in controlling pest ectoparasitic sucking lice populations, especially those which cause the irritation, pruritis and pediculosis diseases of humans.

It is an object of the present invention to overcome, the disadvantages and shortcomings of the abovementioned prior art for the control of sucking lice The microbial preparations disclosed in the present invention are effective and nontoxic to man and other vertebrates and therefore safe for the human patients animals and birds under treatment, and for the human applicator. Because the parasitic sucking lice are controlled by a biological, i.e. microbial means, there is a much-reduced risk of resistance developing in the parasitic sucking lice populations. The method of the present invention is effective in the prevention or remedial treatment of such infestations. Other advantages of the present invention will become apparent from the following description wherein, by way of illustration and example, an embodiment of the present invention is disclosed.

SUMMARY OF THE INVENTION

Definitions

The term "Microbial Preparation" means any combination of the cells, and cell components including proteins, spores, membranes, membrane-bound proteins, membrane-enzymes and/or metabolites, free pathogenic metabolites derived from one or more cultures of bacteria and which are instrumental in causing pathology in, and death of, the parasitic sucking lice.

The term "formulation' means final products comprising or containing the above Microbial Preparations either with or without excipients, additives, and synergists, and with or without liquid or solid carriers or fillers.

According to the present invention, although this should not be seen as limiting the invention in any way, there is provided as examples of this invention, the use of a Microbial Preparation of one or more bacteria, for example of the genus *Bacillus* in the manufacture of a formulation as a medicament for the treatment and prevention of sucking lice infestations. For example, the said medicament may be administered for the control of human head lice by application to the hair and scalp of the patient, or applied to the pelage or plumage of an animal or bird for the control of sucking lice on those hosts.

In preference, the lice are sucking lice are those of the Order Phthiraptera;

In preference, the sucking lice are those of the SubOrder Anoplura or Rhynchophthirina.

In preference, the Family of sucking lice is the Pediculidae;

In preference, sucking lice species are *Pediculus humanus capitis, Pthirus pubis*, and *Pediculus humanus corporis*

In preference, the cultures of bacteria are bacilli of the species *Bacillus thuringiensis, Bacillus cereus*, or *Bacillus moritai*

In preference, the medicament is composed of a formulation of a Microbial Preparation derived from one more species of bacilli.

In preference, the Microbial Preparation may contain some or all of the following:—viable or non-viable bacterial cells, bacterial metabolites including enzymes and proteins, lice pathogenic compounds either membrane- or otherwise bound, or as free entities, viable or non-viable bacterial spores.

In preference, the medicament is a formulation containing an effective amount of the Microbial Preparation which may include, among other components described above, approximately 2×108 to 2×1012 viable bacterial spores or cells per gram.

In preference, the medicament is a formulation containing an effective amount of a Microbial Preparation which may include approximately 2×1010 viable spores or cells per gram.

The invention can reside in various formulations, for example a pediculicidal hair conditioner or anti-lice lotion formulation comprising as an active ingredient an effective amount of the Microbial Preparation described above together with various excipients to produce a lotion, a conditioner, or a shampoo. The formulation can then be readily applied to the hair and scalp and/or combed through the infested hair of a patient suffering from pediculosis to eradicate the sucking lice. After the microbial treatment, the dead sucking lice and their nits (eggs) may be removed by use of a conventional nit comb. By this means, the pediculosis is remedied and the patient is spared from suffering the distressing adverse reactions to harsh chemicals concomitant in the prior art treatment regimes.

In a further embodiment of the invention there is a method for killing animal or bird sucking lice and/or their eggs comprising a Microbial Preparation of one or more bacteria, for example of the genus *Bacillus* or a or metabolite thereof, wherein the Microbial Preparation is present in an amount effective to kill sucking lice and/or their eggs; together with a liquid or dust carrier for topical application to the pelage or plumage of the lice infested animal or bird.

The present invention stems from the applicant's discovery of the entomocidal effects of certain bacteria to sucking lice. The complex biochemical mode of action in killing the sucking lice and their nymphs remains only partially known at the present time. The bacterial metabolites, i.e. viable or non-viable bacterial cells, bacterial metabolites including enzymes and proteins, lice-pathogenic compounds either membrane- or otherwise bound, or as free entities and viable or non-viable bacterial spores, are taken in with the food of the lice. The ingested metabolites cause multiple lethal cytopathologies and metabolic disruptions in the lice; a subsequent mode of action is that the ingested viable spores germinate in the lice and cause fatal enteritis or penetrate into the haemolymph and cause fatal septicaemia.

Broadly, according to this invention, the populations of the relevant parasitic sucking lice, such as species of SubOrders Anoplura (=Siphunculata), and Rhynchophthirina are controlled by treating the infested person animal or bird with an effective amount of a pesticidal Microbial Preparation containing or derived from a bacterium of the genus *Bacillus* or a metabolite thereof, as described below.

A further embodiment of this invention is the combination of one or more of the aforementioned implementation and/or application methods and/or one or more Microbial Preparations derived from *Bacillus thuringiensis*, and/or *Bacillus cereus* and/or *Bacillus moritai* strains. Such combinations may be advantageous when employing this invention for control of more than one parasitic sucking louse species or stage and/or parasitic sucking lice on more than one host species. The best effective combination is determined by the bioassay method described below.

More particularly, there is provided a method of preventing or controlling parasitic sucking lice infestations on persons, animals or birds comprising applying to the infested host an effective amount of a Microbial Preparation derived from or comprising a suitable species of bacterium of the genus *Bacillus*, or, more specifically, the species *Bacillus thuringiensis, Bacillus cereus* or *Bacillus moritai.*

In preference, the lice are of the Order Phthiraptera

In preference, the SubOrder is either Anoplura or Rhynchophthirina.

In preference, the family is Pediculidae.

In preference, the *Bacillus* is of the species *Bacillus thuringiensis, Bacillus cereus*, or *Bacillus moritai.*

BRIEF DESCRIPTION OF THE DRAWINGS

By way of example, an employment of the invention is described more fully hereinafter with reference to the accompanying drawings, in which:

FIG. 1 is the molecular structure of the adenine nucleotide thuringiensin.

DETAILED DESCRIPTION OF THE INVENTION

Background

*Bacillus thuringiensis*

The above species of the genus *Bacillus* generally are aerobic, Gram positive spore-forming bacteria. *Bacillus thuringiensis* is distinguished from the closely related *Bacillus cereus* by the production during sporulation of one or more parasporal, crystalline toxins which are insoluble at neutral pH.

In many strains or serotypes of *Bacillus thuringiensis*, the parasporal crystalline toxins when ingested by insects which possess the highly alkaline gut pH and proteolytic enzymes necessary to dissolve the crystalline toxins and have compatible receptor sites, may be highly toxic to those insects These crystalline toxins have been called the *Bacillus thuringiensis* "delta-endotoxins" or "*Bacillus* thuringiensin toxins" by some authors. These "*Bacillus* thuringiensin toxins' are merely a coincidental result of *Bacillus thuringiensis* sporulation. They are not produced by *Bacillus cereus* and are not lousicidal.

Production of the Microbial Preparations

The following examples set forth details of production of the Microbial Preparations. It should be understood that the specific materials and techniques set forth hereinafter are exemplary only and may vary according to circumstances, so that the following is presented as illustrative, but not restrictive, of the present invention.

The selected strain of *Bacillus* may be produced by standard or conventional fermentation procedures, for example by growing the cells in a suitable liquid medium in a stirred fermenter. During production by fermentation, for example, the following parameters are maintained: pH=7.2; pO2=70-90%; temperature=32.5° C. In general, the above *Bacillus* species are not nutritionally fastidious, and a wide variety of conventional bacterial fermentation media and fermentation parameters may be used.

The production of the Microbial Preparation may follow one of two pathways:—
Production Pathway 1.

The fermentation broth or culture is harvested when the *Bacillus* cells are in the vegetative stage, prior to sporulation. The timing of this harvesting will depend on the *Bacillus* strain under culture and on the fermentation medium and parameters used. In general, harvesting will occur when the cell population reaches the "plateau" or stationary stage of the fermentation—typically at 7 to 10 hours' post-inoculation if an inoculum of 10% of fermenter volume containing $5 \times 10^9$ cells per milliliter is used. The harvested material includes the *Bacillus* cells, cell membranes and fermentation broth metabolites and bacterial metabolites, both free and membrane-bound. Harvesting may be accomplished by one or more standard procedures such as centrifugal separation, filtration, co-precipitation or membrane concentration. The harvested material, in the form of a slurry or cake, which includes the vegetative *Bacillus* cells and the fermentation broth metabolites, etc. constitutes the active ingredient or Microbial Preparation, which is then formulated with conventional excipients to form formulations such as aqueous, non-aqueous or emulsifiable concentrates or lotions, a dispersible suspension, or a shampoo.

Alternatively, the harvested bacterial material is dried by one or more conventional processes such as vacuum drying, spray drying, freeze-drying or by air-drying the harvested material after co-precipitation by the addition of two volumes of acetone. Following homogenisation of the dried material to a fine powder, the material, which constitutes the active ingredient or Microbial Preparation, is then formulated with conventional excipients to form formulations such as aqueous, non-aqueous or emulsifiable concentrates or lotions, a dispersible suspension, a shampoo, or a wettable powder.

Alternatively, the above described harvested dry material, which constitutes the active ingredient or Microbial Preparation, may be thoroughly mixed, milled or blended with a carrier dust, such as finely powdered talc, bentonite, kaolin or celite and other excipients or additives to produce a dust or powder formulation for application to the hair, pelage or plumage of lice-infested hosts.
Production Pathway 2.

After about 28 to 30 hours fermentation and following sporulation, the bacterial culture is harvested by one or more standard procedures, eg by centrifugal separation, filtration, co-precipitation or membrane concentration. The harvested material includes the sporulated *Bacillus* cells, cell membranes, spores, proteins, enzymes and fermentation broth metabolites and bacterial metabolites, both free and membrane-bound.

Harvesting may be accomplished by one or more standard procedures such as centrifugal separation, filtration, co-precipitation or membrane concentration. The harvested material, in the form of a slurry or cake, which includes the sporulated *Bacillus* cells, cell membranes, spores, proteins, enzymes and fermentation broth metabolites, and bacterial metabolites, both free and membrane-bound, constitutes the active ingredient or Microbial Preparation, which is then formulated with conventional excipients to form formulations such as aqueous, non-aqueous or emulsifiable concentrates or lotions, a dispersible suspension, or a shampoo.

Alternatively, the harvested bacterial material is dried by one or more conventional processes such as vacuum drying, spray drying, freeze-drying or by air-drying the harvested material after co-precipitation by the addition of two volumes of acetone. Following homogenisation of the dried material to a fine powder, the material, which constitutes the active ingredient or Microbial Preparation, is then formulated with conventional excipients to form formulations such as aqueous, non-aqueous or emulsifiable concentrates or lotions, a dispersible suspension, a shampoo, or a wettable powder Alternatively, the harvested dry material, which constitutes the active ingredient or Microbial Preparation, may be thoroughly mixed, milled or blended with a carrier dust, such as finely powdered talc, bentonite, kaolin or celite and other excipients or additives to produce a dust or powder formulation for application to the hair, pelage or plumage of lice-infested hosts.
Mode of Action of the Invention
Production Pathway 1.

The selected strains of *Bacillus thuringiensis*, *Bacillus cereus* and *Bacillus moritai* produce a complex of metabolites, such as proteins, proteolytic enzymes and nucleotides, in their vegetative growth stages. Some of these metabolites are membrane-bound and many may be found by bioassay to be pathogenic to sucking lice In some cases, the entomopathogenic adenine nucleotide thuringiensin may be produced. The nucleotide thuringiensin is a potent inhibitor of RNA polymerase, an essential enzyme in the louse, and if present, can be a contributor to the lousicidal effect of the Microbial Preparations. However, as also provided herein, Microbial Preparations without thuringiensin also are effective in killing sucking lice.

When ingested by the pest sucking lice, the pesticidal effect of these metabolites and bacterial metabolites, both free and membrane-bound, plus, where it occurs, the invasion of the lice' alimentary canal by the *Bacillus thuringiensis*, *Bacillus cereus*, or *Bacillus moritai* cells, causes the death by metabolic disruption, enteritis or septicaemia. In this way, the sucking louse infestation is killed so that the disease, pruritis and irritation caused by the sucking lice are controlled.
Mode of Action of the Invention
Production Pathway 2.

The components of the Microbial Preparation include sporulated cells, spores, residual vegetative cells, cell membranes, proteins and metabolites such as proteolytic and glycolytic enzymes, nucleotides, and cellulytic peptides and enzymes bound to the cell membranes. In various combinations, these components are potent lousicidal agents for control of sucking lice.

When ingested by the pest sucking lice, the pesticidal effect of these metabolites and bacterial metabolites, both free and membrane-bound, plus, where it occurs, the invasion of the lice' alimentary canal by the *Bacillus thuringiensis, Bacillus cereus,* or *Bacillus moritai* cells and germinated spores, causes the death by metabolic disruption, enteritis or septicaemia. In this way, the sucking louse infestation is killed so that the disease, pruritis and irritation caused by the sucking lice are controlled.

Selection of the Suitable Bacteria by Means of Bioassay

Suitable bacteria are those having anti-sucking lice activity. The selection of candidate strains of the above said *Bacillus* species for anti-sucking lice activity is made by employing appropriate bioassays as described hereinafter.

The microbial strains employed in this invention are determined by bioassay. Serial concentrations or dilutions of microbial preparations and/or formulations are administered to target sucking lice in one or more appropriate bioassay systems, such as the examples described below. The bioassays consist of treating or exposing replicated samples consisting of numbers of the pest sucking lice to a graded range of dilutions or doses of the Microbial Preparations or components thereof or formulations derived from the candidate bacterial strains. In general, no less than sixty sucking lice per replicate, per dose are used, and no less than five graded dose levels are tested with a minimum of two, and preferably, four replicates of each dose.

A similar number or sample of sucking lice are not treated or exposed to the Microbial Preparation but are otherwise kept under identical bioassay conditions. These untreated sucking lice constitute a reference to ensure that undue sucking lice mortality has not occurred as a result of handling injuries or unsuitable bioassay conditions.

From the resulting sucking lice mortality data, the corrected LD50, LD99 LC50, LC99 and/or LT50, and LT99 is calculated as required. These corrections, for example by Abbott's formula and mortality calculations are in general and widespread use and will be well known to persons familiar with bioassays In general, for a given louse species, the bacterial strain showing the highest potency—i.e. the lowest LD50, LD99, LC50, LC99 and/or most rapid sucking lice mortality—i.e. the lowest LT50, and LT99 is selected as the Microbial Preparations or components thereof or formulations to be used for implementation of this invention for control of that sucking louse species.

For each target species of sucking lice, preliminary bioassays and subsequent bioassays are made along similar lines, but on different, appropriate substrates and on the appropriate hosts. For example, in these bioassays, the doses derived from the candidate bacterial strains may be administered to the sucking lice living on a substrate such as encapsulated blood, simulated skin with or without hair, pelage or plumage as appropriate, or skin scrapings of the host. Depending on the target species of sucking lice, serum may be added to the bioassay system to reduce mortality caused by starvation, which could otherwise confound the results. As mentioned above, sucking lice mortality is measured, the corrected LD50, LD99 LC50, LC99 and/or LT50, and LT99 calculated and, in general, the most potent bacterial strain used for the implementation of this invention for control of that sucking louse species on that host.

Where appropriate, and following successful performance in artificial diet and simulated encapsulated blood, pelage, fleece or plumage bioassays, the Microbial Preparations are bioassayed on the host person, animal or bird. This generally involves topical treatment of the sucking lice-infested person, animal or bird with the Microbial Preparation or formulation under test. The numbers or density of sucking lice are recorded before and after treatment of the person or host with the microbial preparation or formulation. The results are read subsequently as the corrected LD50, LD99 LC50, LC99 and/or the LT50, and LT99 rate of mortality of the sucking lice over time, or duration of prevention of re-establishment of infestation also is recorded. By this means, and in the light of the bioassay results, the selection and effective amount of the Microbial Preparation is determined.

Method of Application of the Invention

The method of application used to effect the treatment may vary according to the species and developmental stage of the sucking lice being controlled, the host species, and sites of sucking lice infestation, the environmental conditions or circumstances and the physical nature of the microbial preparation being employed.

To accommodate the wide range of application methods required, the Microbial Preparations can be formulated as aqueous or non-aqueous concentrates, emulsions, lotions or liquid shampoos, or as wettable powders suitable for application with or without dilution as a shampoo, a spraying, jetting or dipping liquid or as a powder or dust. For example, and as instructed below, when controlling human head lice, *Pediculus humanus* capitis the Microbial Preparation can be formulated and applied to the hair and scalp as a lotion or shampoo or as a spray-on formulation. For other applications, for example the control of sucking lice on birds, the Microbial Preparation may be incorporated in an inert carrier material and applied in the form of a powder or dust.

In order to further explain the invention, reference is now made to specific examples of the method of the invention.

In a first embodiment, the hair and scalp of persons infested with human head sucking lice, *Pediculus humanus* capitis are treated with a lotion, shampoo or spray-on formulation comprising of a liquid containing an effective concentration of a Microbial Preparation derived from one or more selected strains of bacteria of the genus *Bacillus*, specifically *Bacillus thuringiensis, Bacillus cereus* or *Bacillus moritai*, The liquid formulations contain, or are derived wholly or in part from, one or more of the aforementioned Microbial Preparations either alone or augmented by additives, and/or excipients.

For example, the Microbial Preparation may be formulated together with a lotion base which functions as a convenient vehicle for application of the Microbial Preparation on to the lice-infested person. Without limitation of embodiment of the invention, examples of such formulation bases may contain emulsifiers such as glyceryl stearate or sorbitol isostearate, carriers such as polyglycol esters, polyglycol ethers or cetyl alcohol, and additives such as behentrimonium chloride. A mild detergent such as ammonium laureth sulphate may be included to cleanse the hair and scalp. Benign lipids such as wheat germ oil or wheat bran lipids (Biobranil®) may be included in the final formulation to improve the combing qualities of the treated hair. The resulting lotion or shampoo containing an effective amount of the Microbial Preparation is applied to the hair and scalp of lice-infested persons and thoroughly distributed throughout the hair by combing.

Methods of Implementation of the Invention

The exposure of the parasitic sucking lice to the *Bacillus thuringiensis, Bacillus cereus* or *Bacillus moritai* pesticidal entities and metabolites in the Microbial Preparation is achieved by one or more of the following methods of implementation of this invention.

Implementation Method 1—Use of Metabolite Preparations

The Microbial Preparation or formulation applied as described above to the human, animal or bird host contains an effective quantity of the active membrane-bound and free metabolites also described above so that when ingested by the parasitic sucking lice, the sucking lice are killed and/or unable to reproduce. These entomocidal metabolites originate in the fermenter broth harvested with the selected *Bacillus thuringiensis, Bacillus cereus* or *Bacillus moritai* strain. In some implementations, the pesticidal effect of the metabolites may be augmented (see below) by the invasion of the sucking lice alimentary canal and haemocoel by invading *Bacillus* cells either present in the formulation or derived from spores present in the formulation. The death and hence elimination of the parasitic sucking lice is the means whereby the infestation is controlled and the disease, pediculosis in the case of humans, is remedied.

Implementation Method 2—Use of Vegetative Cell Preparations

The Microbial Preparation or formulation contains in addition to the components of Implementation Method 1, viable, vegetative cells of one or more of the selected *Bacillus thuringiensis, Bacillus cereus* or *Bacillus moritai* strains. After application as described above on to the human, animal or bird, these viable cells persist on the host, with or without the aid of nutrients added to the applied formulation. These viable cells, applied in very close proximity to, the feeding sites of the parasitic sucking lice, produce the pesticidal metabolites in situ i.e. the enzymes and other metabolites described above.

These metabolites then diffuse or move into the feeding sites where they are ingested by, and kill, the parasitic sucking lice. In some implementations, the pesticidal effect of the metabolites may be augmented by the invasion of the sucking lice' alimentary canal and haemolymph by the *Bacillus* cells, causing lethal septicaemia. The death and elimination of the parasitic sucking lice is the means whereby the infestation is controlled and the disease, pediculosis in the case of humans, is remedied.

Implementation Method 3—Use of Spore Preparations

The Microbial Preparation or formulation contains in addition to the components of Implementation Method 1 and 2, viable spores of one or more of the selected *Bacillus thuringiensis, Bacillus cereus* or *Bacillus moritai* strains. These spores may be "potentiated" by heat treatment so that a certain proportion, when wetted, will quickly germinate in the presence of an appropriate inducer. Prior to application on to the infested human, animal, or bird a spore germination inducer, for example as L-alanine, adenosine, glucose or calcium dipicolinate, may be added, if desired, to the microbial preparation or formulation so that the spores rapidly germinate and produce vegetative cells on the treated host.

As in Implementation Method 2, above, these vegetative cells then grow, produce the pesticidal metabolites and so kill the parasitic sucking lice. In some implementations, the pesticidal effect of the metabolites may be augmented by the invasion into the haemolymph of the sucking lice by the *Bacillus* cells, or cells derived from germinated spores, causing lethal septicaemia. The death and elimination of the parasitic sucking lice is the means whereby the infestation is controlled and the disease, pediculosis in the case of humans, is remedied.

Implementation Method 4—Use of Spore and Entomocidal Protein Preparations

The Microbial Preparation or formulation contains viable spores and membrane-bound and/or free entomocidal peptides enzymes or proteins of the selected *Bacillus thuringiensis, Bacillus cereus* or *Bacillus moritai* strain. These components are entomocidal by causing death of the sucking lice by massive alimentary canal damage when ingested by the sucking lice. The spores may be "potentiated" by heat treatment so that when wetted, they will quickly germinate in alimentary canal of the sucking lice, invade the haemolymph and cause death of the sucking lice by septicaemia and the disease, pediculosis in the case of humans, is remedied.

In an actual example of this embodiment, an eleven-year old male child with a history of acute pediculosis caused by persistent infestations of head lice was treated twice with a shampoo formulated as described in Implementation Method 4 above. The treatments were applied ten days apart. The purpose of second treatment was to control head lice that were in the egg (nit) stage at the time of the first treatment. No adverse reactions were experienced by the child and the child's head lice infestation was completely eradicated and his pediculosis disease was remedied.

Notwithstanding that the embodiment of the invention herein shown and described is one conceived to be a most practical and preferred embodiment, it is recognized that departures can be made within the scope of the invention, which is not to be limited to the details described herein but it is to be accorded the full scope of the appended claims so as to embrace any and all equivalent embodiments, so that various modifications may be made in details of process, parameters of operation etc without departing from the scope and ambit of the invention.

The invention claimed is:

1. A composition for killing human sucking lice of an order Phthiraptera and a sub order of either Anoplura or Rhynchophthirina and/or their eggs comprising:

a liquid microbial preparation derived from a bacterium of the genus *Bacillus* including a combination of the bacterium cells, and cell components, the cell components comprising proteins, spores, membranes, membrane-bound proteins, membrane-enzymes and membrane-bound metabolites, and free pathogenic metabolites thereof, wherein the microbial preparation is prepared without an acetone drying step;

wherein the membrane-bound proteins, membrane-enzymes or membrane-bound metabolites of a bacterium of the genus *Bacillus* or a combination thereof are present in an amount effective to kill the human sucking lice and/or their eggs; and a carrier for topical application, wherein the *Bacillus* bacterium is not a thuringiensin producing bacterium.

2. The composition of claim 1, wherein the sucking lice of the sub order Anoplura is of a Pediculidae family.

3. The composition of claim 2, wherein the *Bacillus* is of the species *Bacillus thuringiensis, Bacillus cereus*, or *Bacillus moritai.*

4. The composition of claim 3, wherein the composition contains between approximately $2\times10^8$ and $2\times10^{12}$ viable spores or cells per gram.

5. The composition of claim 4, wherein the composition contains approximately $2\times10^{10}$ viable spores or cells per gram.

* * * * *